(12) United States Patent
Yoneda (10) Patent No.: US 7,052,162 B2
(45) Date of Patent: May 30, 2006

(54) ILLUMINATING UNIT

(75) Inventor: Kenji Yoneda, Kyoto (JP)

(73) Assignee: CCS, Inc., Kyoto (JP)

( * ) Notice: Subject to any disclaimer, the term of this patent is extended or adjusted under 35 U.S.C. 154(b) by 206 days.

(21) Appl. No.: 10/616,626

(22) Filed: Jul. 10, 2003

(65) Prior Publication Data

US 2004/0022072 A1    Feb. 5, 2004

(30) Foreign Application Priority Data

Jul. 16, 2002    (JP)    ............................ P2002-206980

(51) Int. Cl.
*F21V 17/00*    (2006.01)

(52) U.S. Cl. ...................... 362/455; 362/556; 362/581; 385/35

(58) Field of Classification Search ................. 362/33, 362/455, 556, 581; 385/33, 35
See application file for complete search history.

(56) References Cited

U.S. PATENT DOCUMENTS 5,268,977 A * 12/1993 Miller .......................... 362/581
6,523,984 B1 * 2/2003 Belfer .......................... 362/581
6,595,674 B1    7/2003 Yoneda
6,832,849 B1 * 12/2004 Yoneda et al. ............... 362/556

* cited by examiner

*Primary Examiner*—Stephen F Husar (57) ABSTRACT

An improved illuminating unit for illuminating a target portion of an object to be illuminated is provided, including: a fiber holding portion having a fiber insert hole holding a light-emitting end portion of an optical fiber; and a lens holding portion located downstream of the fiber holding portion in a light traveling direction, light emitted from a light-emitting end of the optical fiber being directed to the target portion through a lens held by the lens holding portion, wherein: the fiber insert hole comprises an equal-diameter portion having a diameter substantially equal to a diameter of the optical fiber, and a larger-diameter portion having a larger diameter than the equal-diameter portion and opening at one end face of the fiber holding portion, the fiber insert hole holding the optical fiber extending through the equal-diameter portion; and the lens is abutted against the one end face of the fiber holding portion or a forward end face of a fusion-deformed portion of the optical fiber, the fusion-deformed portion being fitted in the larger-diameter portion and resulting from fusion deformation of a leading end portion of the optical fiber projecting from the equal-diameter portion.

13 Claims, 13 Drawing Sheets

ILLUMINATING UNIT

BACKGROUND OF THE INVENTION

1. Field of the Invention

The present invention relates to illuminating units for illuminating products with light supplied through optical fiber to inspect the products for their outward appearances, flaws and the like or detect alignment marks and the like.

2. Description of the Related Art

One known illuminating unit is constructed to illuminate a work with light supplied from a light source unit, such as a halogen lamp, through plural optical fibers, as disclosed in Japanese Patent Laid-Open Gazette No. HEI 5-248820. Such an illuminating unit does not incorporate any light source therein and hence can be reduced in size and weight and can offer improved degree of freedom of installation and the like.

Recently, there are increasing demands for precise inspection requiring bright illumination upon a very small object to be inspected such as a semiconductor chip or upon a very small portion of a work such as a portion of such a semiconductor chip soldered to a printed circuit board. For this reason, the need has arisen for illuminating a portion of concern efficiently with more condensed and brighter light.

In this respect, however, prior-art illuminating units of this type are unsatisfactory in terms of focusing area, condensing efficiency and the like. For example, an illuminating unit disclosed in Japanese Patent Laid-Open No. HEI 5-199442 condenses light only radially of a ring lens and does not condense light circumferentially of the ring lens, though is capable of preventing light from escaping externally by virtue of the ring lens. Thus, this illuminating unit cannot sufficiently focus light onto a very small area.

In the case where light is condensed with lenses attached to optical fibers one by one, on the other hand, it is required that the positional relations between the light-emitting ends of the respective optical fibers and the lenses be uniform throughout. This is because non-uniform positional relation makes condensing of light unfavorable and might give rise to uneven illuminance on a portion illuminated. As the number of optical fibers used increases, it becomes more difficult to establish uniform positional relation between all the optical fiber used and the respective lenses.

Accordingly, it is a major object of the present invention to solve the aforementioned problems at a time by providing an illuminating unit having a simplified structure capable of setting uniform positional relations between the light-emitting ends of optical fibers and respective lenses very easily and precisely as well as of improving light transmission efficiency therebetween as much as possible.

SUMMARY OF THE INVENTION

In accordance with one aspect of the present invention, there is provided an illuminating unit for illuminating a target portion of an object to be illuminated, comprising: a fiber holding portion having a fiber insert hole holding a light-emitting end portion of an optical fiber; and a lens holding portion located downstream of the fiber holding portion in a light traveling direction, light emitted from a light-emitting end of the optical fiber being directed to the target portion through a lens held by the lens holding portion, wherein: the fiber insert hole comprises an equal-diameter portion having a diameter substantially equal to a diameter of the optical fiber, and a larger-diameter portion having a larger diameter than the equal-diameter portion and opening at one end face of the fiber holding portion, the fiber insert hole holding the optical fiber extending through the equal-diameter portion; and the lens is abutted against the one end face of the fiber holding portion or a forward end face of a fusion-deformed portion of the optical fiber, the fusion-deformed portion being fitted in the larger-diameter portion and resulting from fusion deformation of a leading end portion of the optical fiber projecting from the equal-diameter portion.

The "one end face of the fiber holding portion", as used herein, refers to an end face of the fiber holding portion located downstream in the light traveling direction and may include the open end of the larger-diameter portion.

In the illuminating unit thus constructed, the fusion-deformed portion is located continuous with the light-emitting end of the optical fiber and has a fixed shape fitted in the larger-diameter portion. Thus, the distance between the light-emitting end of the optical fiber and the lens abutted against the forward end face of the fusion-deformed portion or the one end face of the fiber holding portion can be set precisely and easily. When illuminating a predetermined target portion of an object from around, for example, by an arrangement comprising a plurality of optical fibers disposed annularly, light rays emitted from the respective optical fibers can be focused uniformly and equidistantly and hence can be focused on the predetermined target portion advantageously without any difficulty.

Further, the forward end face of the fusion-deformed portion can be turned into a mirror surface without the need for polishing or grinding or the like and, hence, light transmission at the forward end face will not be impeded. Thus, the step of polishing the end face can be eliminated.

Moreover, if the lens is abutted against the forward end face of the fusion-deformed portion, the lens will resist to a force working to drive the optical fiber into the fiber holding portion toward the light traveling direction, while the larger-diameter portion will resist to a force working to pull the optical fiber out of the fiber holding portion. Thus, the optical fiber can reliably be held by the fiber holding portion without the need to bond the optical fiber in the fiber insert hole or a like need.

For preventing the light transmission efficiency from being affected, the larger-diameter portion is desirably shaped to have an inner periphery clear of light that is divergently emitted from the light-emitting end of the optical fiber.

Specific embodiments of the illuminating unit allowing easy assemblage thereof to be achieved include an arrangement wherein: the lens holding portion has a lens holding hole accommodating and holding the lens therein; and the fiber holding portion is shaped columnar having a sectional configuration same as the lens holding hole and defining the fiber insert hole axially extending therethrough, the fiber holding portion being fitted in the lens holding hole on a side opposite away from the target portion in a manner to abut the lens against the forward end face of the fusion-deformed portion or the one end face of the fiber holding portion.

Where the lens has a larger diameter, the diameter of the lens holding hole for holding the lens becomes larger accordingly. However, the fiber holding portion requires relatively precise machining for its shaping and must permit the optical fiber to be inserted therethrough and, hence, changing the shape of the fiber holding portion to meet the lens holding hole will impose a burden on the production equipment and is not preferable even from the view point of cost and the like. For a standardized fiber holding portion to accommodate to different lens holding holes, it is preferred that the illuminating unit further comprise a cylindrical adapter having an inner periphery capable of fitting around the fiber holding portion without play therebetween and an outer periphery capable of fitting into the lens holding hole without play therebetween, provided the fiber holding portion has a smaller diameter than the lens holding portion.

In this case the adapter may be formed with a tapered surface for abutting and fixing the lens on a side closer to the target portion. This feature is more preferable because the lens can be held stably.

A specific embodiment of the illuminating unit, which makes the effect of the present invention particularly outstanding, further comprises an enclosure having an observation bore for allowing observation of the target portion of the object, wherein: the enclosure defines a plurality of discrete fiber insertion holes equispaced in a peripheral edge portion surrounding the observation bore and holding respective optical fibers; and the lens holding portion holds a plurality of lenses in a one-to-one correspondence with the optical fibers.

For more effective focusing, this arrangement may further comprise a single second lens for refracting light rays outgoing from the respective lenses to gather the light rays onto the target portion, the second lens being located between the plurality of lenses and the target portion and having an annular shape defining a central hole extending therethrough coaxially with the observation bore.

Specific embodiments of the lens holding portion include one having a ring shape defining a plurality of discrete lens holding holes located circumferentially.

For the lens holding portion to be more simplified in construction, the lens held by the lens holding portion is preferably spherical.

The fusion-deformed portion is not necessarily needed. Any arrangement capable of precisely and easily setting the distance between the light-emitting end of the optical fiber and the lens can produce the essential effect of the present invention. Specifically, an illuminating unit of such an arrangement comprises: a fiber holding portion having a fiber insert hole holding a light-emitting end portion of an optical fiber; and a lens holding portion located downstream of the fiber holding portion in a light traveling direction, light emitted from a light-emitting end of the optical fiber being directed to the target portion through a lens held by the lens holding portion, wherein: the fiber insert hole comprises an equal-diameter portion having a diameter substantially equal to a diameter of the optical fiber, and a larger-diameter portion having a larger diameter than the equal-diameter portion and opening at one end face of the fiber holding portion, the fiber insert hole holding the optical fiber extending through the equal-diameter portion with the light-emitting end thereof coinciding with a forward end of the equal-diameter portion; and the lens is abutted against the one end face of the fiber holding portion.

The foregoing and other objects, features and attendant advantages of the present invention will become more apparent from the reading of the following detailed description of the invention in conjunction with the accompanying drawings.

DETAILED DESCRIPTION OF THE PREFERRED EMBODIMENTS

The present invention will now be described in detail with reference to the accompanying drawings wherein like reference characters designate like or corresponding parts throughout several views.

Figure 1:
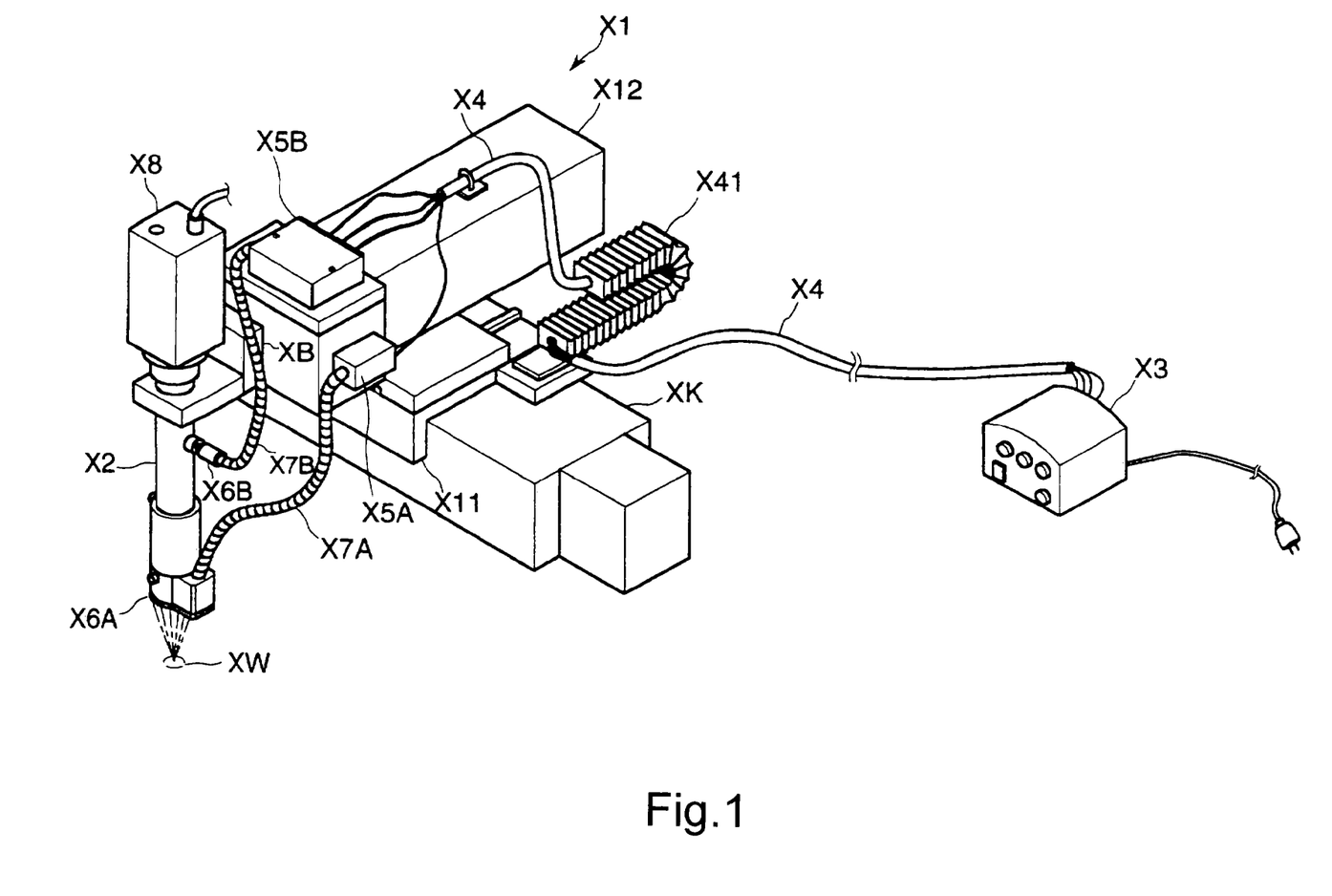
FIG. 1 is an overall perspective view of a product inspection system including an illuminating unit according to one embodiment of the present invention.

Referring to FIG. 1, there is shown a product inspection system including an illuminating unit X6A according to one embodiment of the present invention. The product inspection system utilizes an XY stage X1 as a movable support member that is biaxially movable in a horizontal plane, i.e., horizontally movable along X-axis and Y-axis. The product inspection system includes a light path tube X2 supported by the XY stage X1, an image pick-up device X8 for imaging a target portion XW of a work to be illuminated through the light path tube X2, an electric power source X3 installed separately from the XY stage X1, LED light source devices X5A and X5B to be supplied with electric power from the electric power source X3 through a robot cable X4, the illuminating unit X6A vertically slidably mounted at the lower end of the light path tube X2 for illuminating the target portion XW with light from around (sidewardly directed light), a second illuminating unit X6B mounted at the upper end of the light path tube X2 for illuminating the target portion XW with light from above (downwardly directed light) through optical members provided within the light path tube X2, and optical fiber bundles X7A and X7B formed from resin and serving as light guides for guiding light from the LED light source devices X5A and X5B to the illuminating units X6A and X6B, respectively.

When a work such as a printed circuit board is conveyed to a predetermined position by a conveyor unit not shown, the image pick-up device 8 reads, for example, an alignment mark of the work, causes a non-illustrated image recognition section to recognize the mark and calculates the positional information about the mark. In turn, the XY stage X1 is automatically controlled based on the positional information thus calculated so that the light path tube X2 is positioned just above a target portion XW of the work to be illuminated. As a result, the target portion XW is illuminated from around and from just above with light rays emitted from the respective illuminating units X6A and X6R, whereby the image pick-up device 8 can obtain a favorable image of the target portion XW with high definition and without shadow. In reverse, the positional information about the work can be obtained by controlling the position of the XY stage X1 in this way. Thus, the product inspection system can be utilized as a work position determining system. The product inspection system can also be utilized in reading bar codes or the like.

Figure 2:
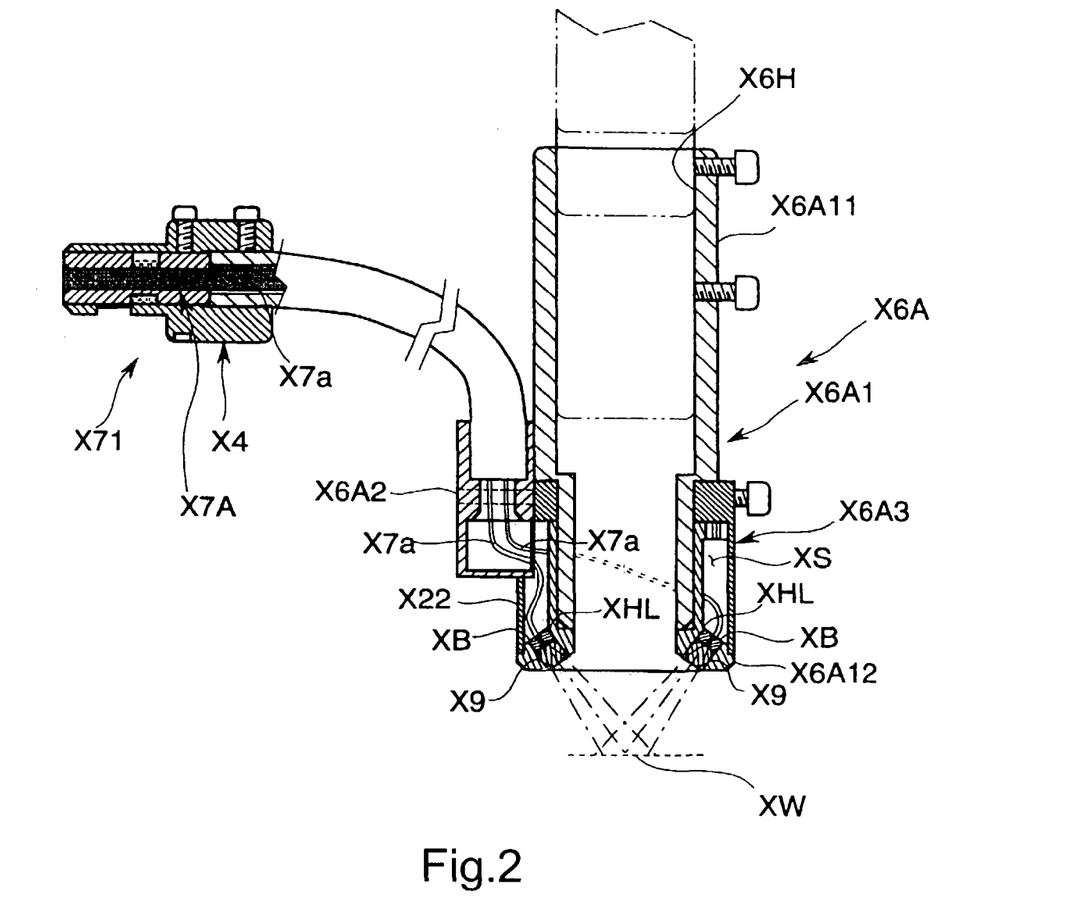
FIG. 2 is a vertical sectional view of the same illuminating unit.
Figure 3:
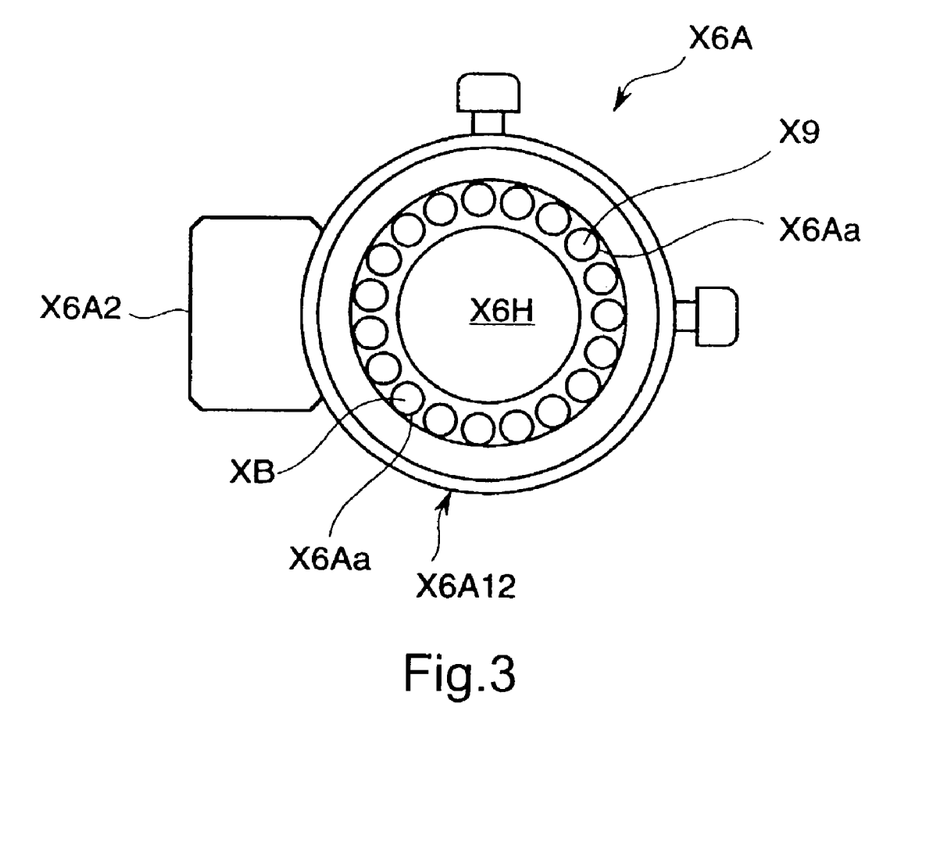
FIG. 3 is a bottom plan view of the same illuminating unit.

The illuminating unit X6A according to this embodiment is adapted to illuminate the target portion XW from around with light supplied from the LED light source device X5A through the optical fiber bundle X7A. The illuminating unit X6A is of a very small size having an outer diameter of about 10 to about 30 mm. The illuminating unit X6A, which is attached to the end of the light path tube X2 on the target portion side, i.e. the lower end of the light path tube X2, comprises a cylindrical enclosure X6A defining an observation bore X6H for observation of the target portion XW, a fiber bundle holding portion X6A2 holding one end of the optical fiber bundle X7A, and a cover member X6A3 covering an outer peripheral surface of the enclosure X6A1, as shown in FIGS. 2 to 4.

Specifically, the enclosure X6A1 comprises a cylindrical enclosure body X6A11 having an inner periphery defining the observation bore X6H, and a ring-shaped lens holding portion X6A12 fitted around the enclosure body X6A11 and protruding radially outwardly like a collar from the peripheral edge portion defining the opening of the observation bore X6H, that is, from the end portion of the enclosure body X6A11 on the target portion XW side.

The collar portion of the lens holding portion X6A12 defines circumferentially equispaced plural lens holding holes each extending at a predetermined angle with respect to the axis of the observation bore so that the central axis thereof passes through the center point of the target portion to be illuminated.

Figure 4:
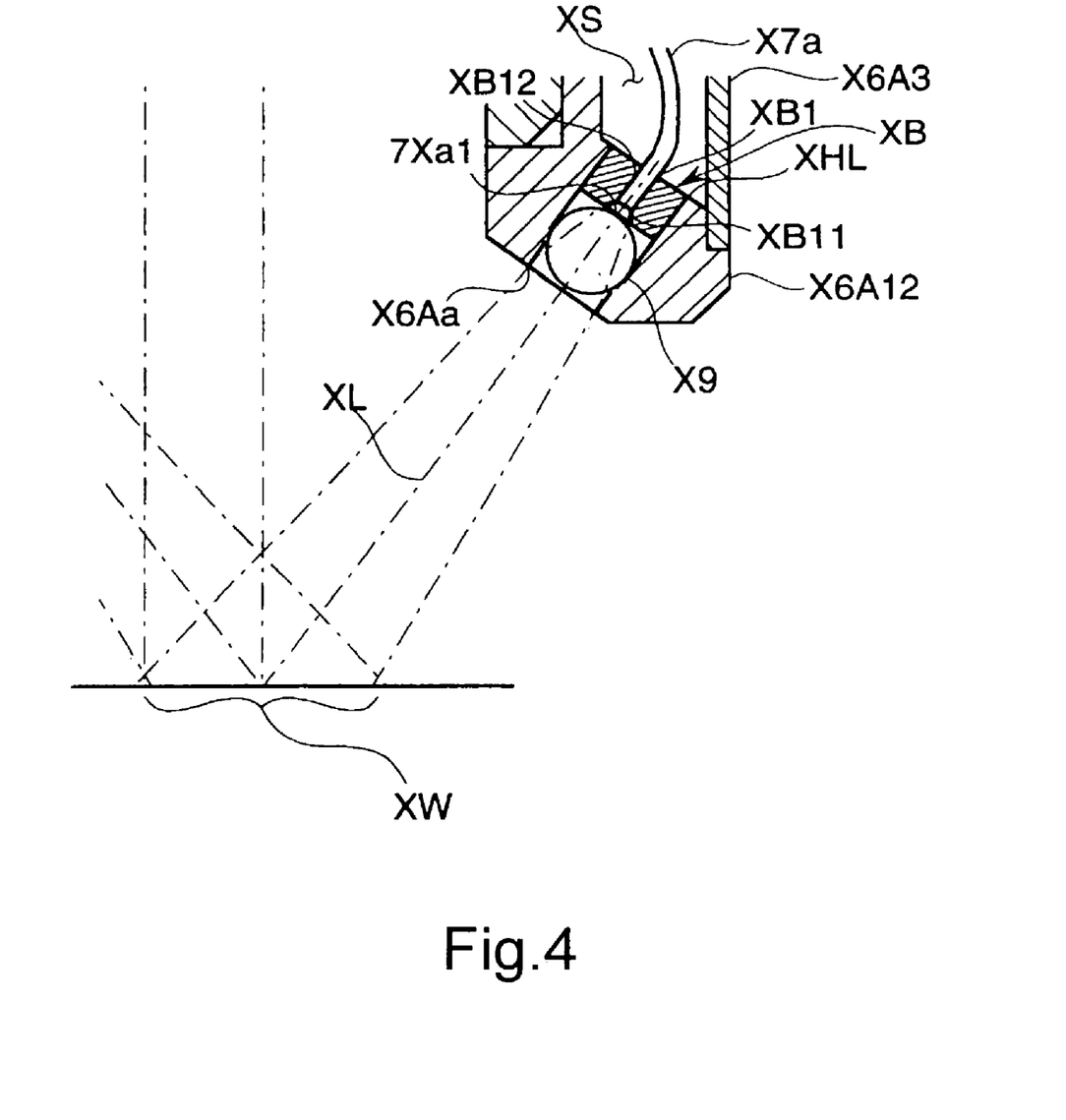
FIG. 4 is a fragmentary sectional view of the same illuminating unit.

As shown in the enlarged view of FIG. 4, each of the lens holding holes XHL is shaped circular in section and has a diameter equal to or substantially equal to the diameter of a ball lens X9. Ball lens X9 is fitted into each lens holding hole XHL from the side opposite away from the target portion XW side, while the lens holding hole XHL holds the ball lens X9 at one end portion thereof on the target portion XW side. The lens holding hole XHL has a smaller-diameter portion XHL1 having a slightly smaller diameter in the end portion thereof on the target portion XW side, the smaller-diameter portion XHL1 functioning as a come-out preventive portion holding the ball lens X9 so as to prevent it from coming out of the end portion toward the target portion XW side. The opening of the each lens holding hole XHL defined on the target portion XW side XW is an illuminating aperture X6Aa for directing light toward the target portion XW.

In the other end portion of the lens holding portion XHL is fitted a cylindrical fiber holding portion XB having a diameter equal to or substantially equal to the inner diameter of the lens holding portion XHL by force fit or the like. The fiber holding portion XB also serves to prevent the ball lens X9 from coming out of the lens holding portion XHL upwardly. This cylindrical member XB is a molded product of resin such as polyacetal and defines a fiber insert hole XB1 extending therethrough on the central axis thereof. An optical fiber X7a is inserted into and held by the fiber insert hole XB1.

The fiber insert hole XB1 comprises a larger-diameter portion XB11 formed into, for example, a conical shape by spot-facing one end face of the fiber holding portion XB on the target portion XW side, and an equal-diameter portion XB12 having a diameter equal to or substantially equal to the outer diameter of the optical fiber X7a. The leading end portion of the optical fiber X7a inserted through the fiber insert hole XB1 from the equal-diameter portion XB12 side is fusion-deformed by means of a hot plate or the like and this fusion-deformed portion X7a1 is fitted in the larger-diameter portion XB11 so as not to form any clearance therebetween. A virtual light-emitting end X7a2 of the optical fiber 7a comprising a core and a cladding is positioned to coincide with the forward end of the equal-diameter portion XB12. The larger-diameter portion XB11 is flared at an angle equal to or larger than the angle of divergence of light emitted form the light-emitting end X7a2.

Figure 5:
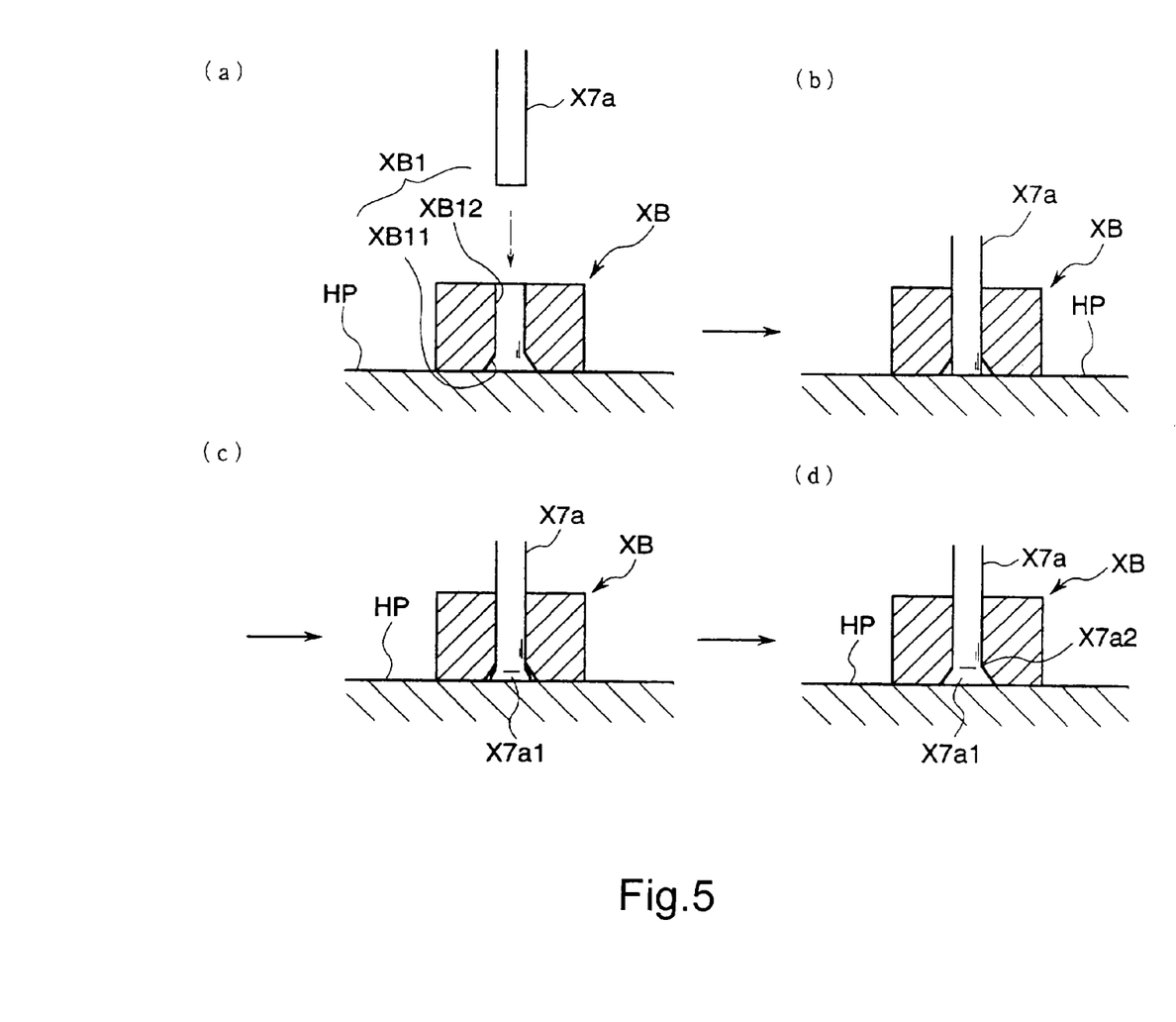
FIGS. 5(a) to 5(d) are schematic views illustrating one process of assemblage of the same illuminating unit including fitting of an optical fiber.
Figure 6:
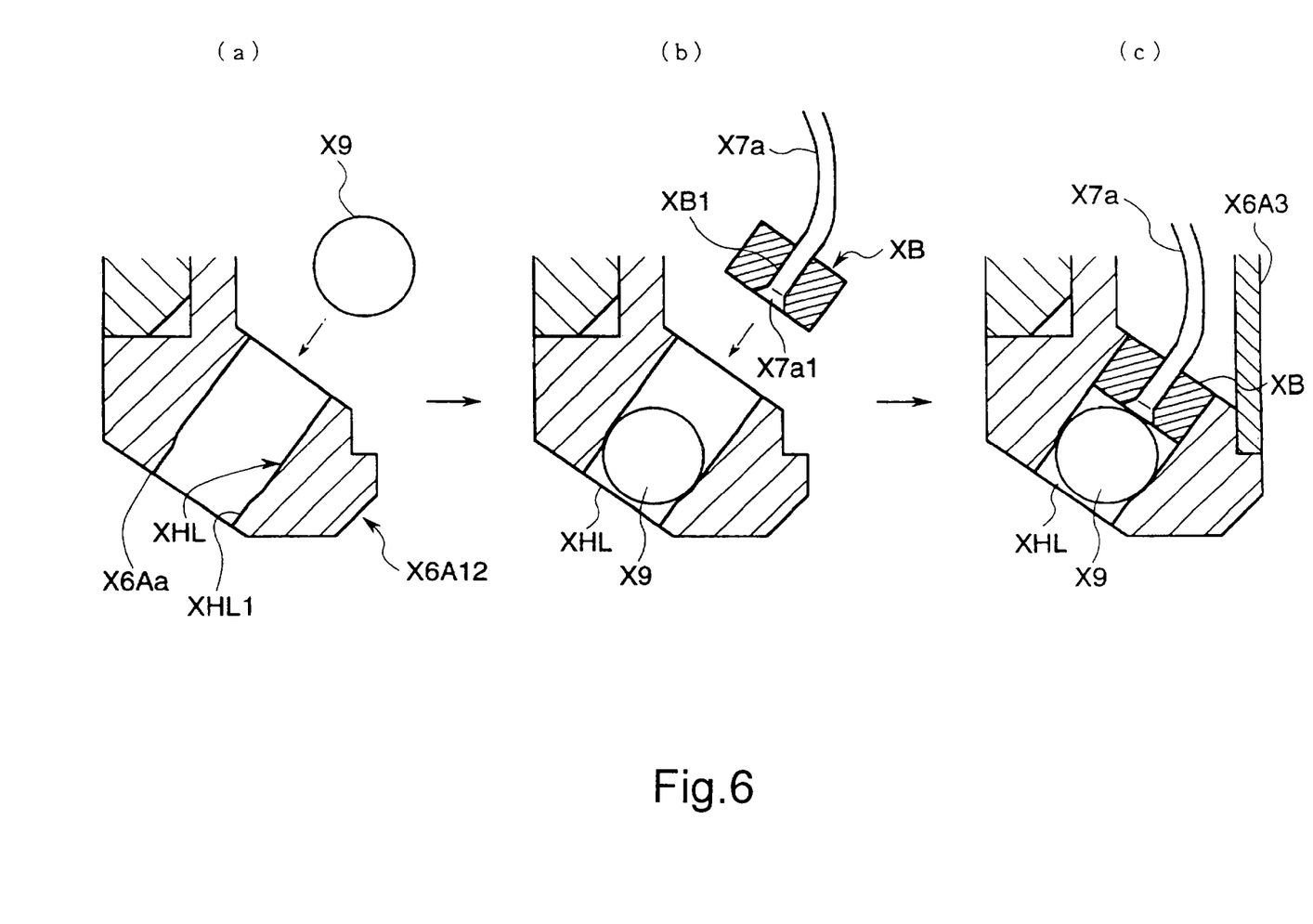
FIGS. 6(a) to 6(c) are schematic views illustrating one process of assemblage of the same illuminating unit including fitting of an optical fiber and a lens.

Referring now to FIGS. 5 and 6, description is made of a process for fitting the optical fiber X7a and the ball lens X9 into respective holding portions.

As shown in FIG. 5(a), first, the fiber holding portion XB is placed on a hot plate HP set at a predetermined temperature causing the optical fiber X7a to fuse with its larger-diameter portion XB11 side end face abutting a flat surface portion of the hot plate HP. Here, the flat surface portion of the hot plate HP is a very smooth mirror surface. In turn, the optical fiber X7a is inserted into the fiber insert hole XB1 from the equal-diameter portion XB12 side so that the leading end of the optical fiber X7a passes through the equal-diameter portion XB12 and reaches the flat surface portion of the hot plate HP, as shown in FIG. 5(b). By so doing, the leading end portion of the optical fiber X7a begins fusing due to heat from the hot plate HP and turns into fusion-deformed portion X7a1 of transparent resin having no boundary between the core and the cladding, as shown in FIG. 5(c). Since the fusion-deformed portion X7a1 gradually extends to fill the larger-diameter portion XB11, the optical fiber X7a is further driven into the fiber insert hole XB1 with a predetermined pressure for a predetermined period of time correspondingly to increasing extension of the fusion-deformed portion X7a1.

By appropriately establishing the temperature of the hot plate HP, the pressure for driving the optical fiber X7a into the fiber insert hole XB1 and the time period for which the optical fiber X7a is to be driven into the fiber insert hole XB1 from the time the leading end of the optical fiber contacts the hot plate HP, the fusion-deformed portion X7a can fill up and fit in the larger-diameter portion XB11 completely without forming any clearance therebetween, with its leading end face becoming flush with the end face of the fiber holding portion XB on the target portion XW side. At the same time therewith, the light-emitting end X7a2 of the optical fiber X7a can be located as spaced a predetermined distance apart from the forward end face of the fusion-deformed portion X7a1 or from the aforementioned end face of the fiber holding portion XB on the target portion XW side; specifically, the light-emitting end X7a2 can be located to coincide with the forward end of the equal-diameter portion XB12 (i.e. the boundary between the equal-diameter portion XB12 and the larger-diameter portion XB11).

Subsequently, as shown in FIG. 6(b), the fiber holding portion XB holding the light-emitting end portion of the optical fiber X7a is fitted into the end portion of the lens holding hole XHL on the side opposite away from the target portion XW side as described above. At that time the forward end face of the fusion-deformed portion X7a1 is abutted against the ball lens X9 as shown in FIG. 6(c).

In this way the ball lenses X9 and the light-emitting ends of respective optical fibers X7a are positioned as confronting each other through respective fusion-deformed portions X7a1 in a one-to-one correspondence so that the axis of the light-emitting end portion of each optical fiber X7a becomes aligned with the optical axis of the corresponding ball lens X9, thereby directing the optical axes of light rays outgoing from respective ball lenses X9 toward a predetermined one point on the target portion XW to illuminate the target portion XW from around. The optical axes of light rays need not necessarily be directed toward a predetermined one point on the target portion XW and may be directed to different points on the target portion XW dispersedly.

As shown in FIG. 2 and other figures, the fiber bundle holding portion X6A2 is attached to the enclosure X6A1 as protruding laterally outwardly and holds one end portion of the optical fiber bundle X7A as described earlier. The optical fibers X7a take the form of a bundle until they reach the fiber bundle holding portion X6A2 where they are separated from each other one by one, and their light-emitting end portions are held in respective fiber holding portions XB1. The other end of the optical fiber bundle X7A is attached to the connector X71 for receiving light emitted from the aforementioned LED light source device X5A.

The cover member X6A3 is shaped cylindrical and mounted on the enclosure X6A1 so as to define a space XS between the cover member X6A3 and a lower outer peripheral surface of the enclosure X6A1 for accommodating and protecting the optical fibers X7a.

In the illuminating unit X6A thus constructed according to this embodiment the fusion-deformed portion X7a1 is formed continuous with the light-emitting end X7a2 of each optical fiber X7a and has a fixed shape for fitting in the larger-diameter portion XB11. For this reason the distance between the light-emitting end X7a2 of each optical fiber X7a and the corresponding lens X9 abutting the forward end face of the fusion-deformed portion X7a1 can be set precisely and easily. Thus, even when the plural optical fibers X7a are arranged annularly, light rays emitted from respective optical fibers X7a can be condensed uniformly and hence can be focused on the target portion XW advantageously without any difficulty.

Further, the forward end face of the fusion-deformed portion X7a1 presents a mirror surface without requiring any process of polishing or the like, which will not give rise to impediment to light transmission at that portion. Thus, the step of polishing or grinding the end face, which would otherwise be required, can be eliminated.

Moreover, since the illuminating unit X6A is constructed to abut the lens X9 against the forward end face of the fusion-deformed portion X7a1, the lens X9 will resist to a force working to drive the optical fiber X7a toward the light traveling direction, while the larger-diameter portion XB11 will resist to a force working to pull the optical fiber X7a in the opposite direction. Thus, the optical fiber X7a can reliably be held by the fiber holding portion XB without the need to bond the optical fiber X7a in the fiber insert hole XB or a like need.

Furthermore, the larger-diameter portion XB11 is flared at an angle equal to or larger than the angle of divergence of light emitted form the light-emitting end X7a2, the inner periphery of the larger-diameter portion XB11 is kept clear of light that is divergently emitted from the light-emitting end of the optical fiber and, hence, the light transmission efficiency at that portion will not be affected.

Additionally, since the fiber holding portion XB is fitted into the lens holding hole XHL after the fitting of the optical fiber X7a into the fiber holding portion XB, the assembling operation can be shared, which makes the manufacture more efficient. Further, the fiber holding portion XB also serves to prevent the ball lens X9 from coming out of the lens holding hole XHL and hence can dispense with an exclusive comeout preventive structure and contribute to simplification of the illuminating unit.

It should be noted that the present invention is not limited to the foregoing embodiment.

Figure 7:
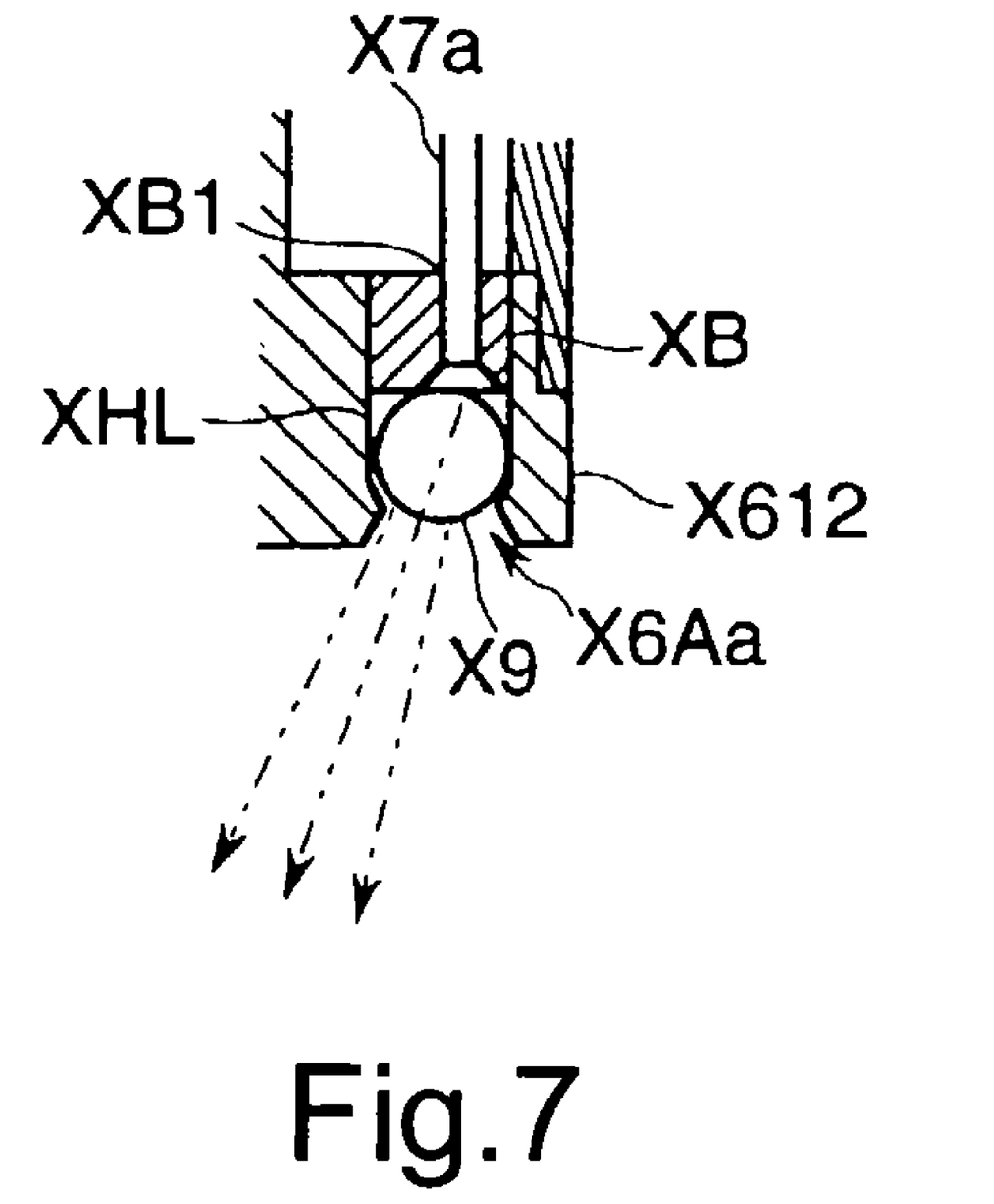
FIG. 7 is a fragmentary sectional view of an illuminating unit according to a variation of the same embodiment.

FIG. 7 is a fragmentary sectional view of an illuminating unit X6 as a variation of the foregoing embodiment wherein the optical axis of lens X9 extends obliquely with respect to the axis of the light-emitting end portion of optical fiber X7a to bend the optical axis of light emitted from the light-emitting end through the lens X9, thereby orienting the optical axis of light toward target portion XW to be illuminated. With this arrangement the axis of the light-emitting end portion of the optical fiber X7a need not necessarily be oriented toward the target portion XW. A specific example of such an arrangement is such that fiber insert hole XH1 is formed to have an axis offset with respect to the central axis of fiber holding portion XB. In this case the lens X9 need not necessarily be abutted against the forward end face of fusion-deformed portion X7a1 and may be abutted against the forward end face of the fiber holding portion XB.

Figure 8:
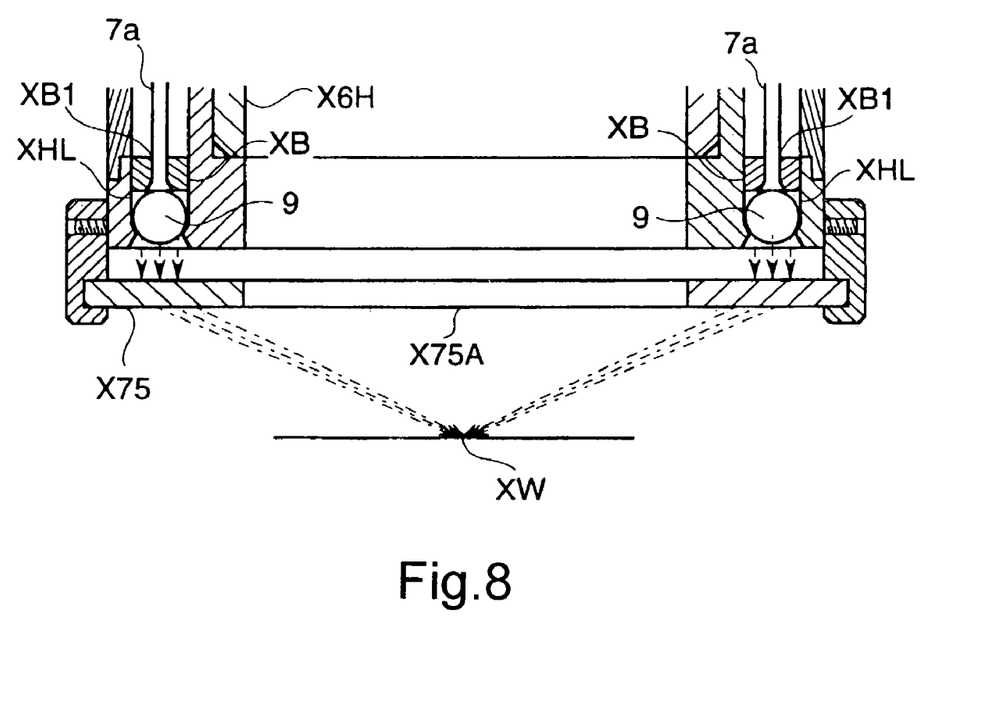
FIG. 8 is a fragmentary sectional view of an illuminating unit according to another variation of the same embodiment.

FIG. 8 shows another variation of the foregoing embodiment wherein a single second condenser lens X75 defining a central opening X75A is provided for further condensing light rays outgoing from respective lenses X9. Though the second condenser lens X75 shown is a Fresnel lens, the second condenser lens X75 may be any suitable lens such as a convex lens. In this variation each of the lenses X9 is preferably a lens adapted to turn light from each optical fiber X7a into parallel rays, taking the condensing function of the second lens X75 into consideration.

Figure 9:
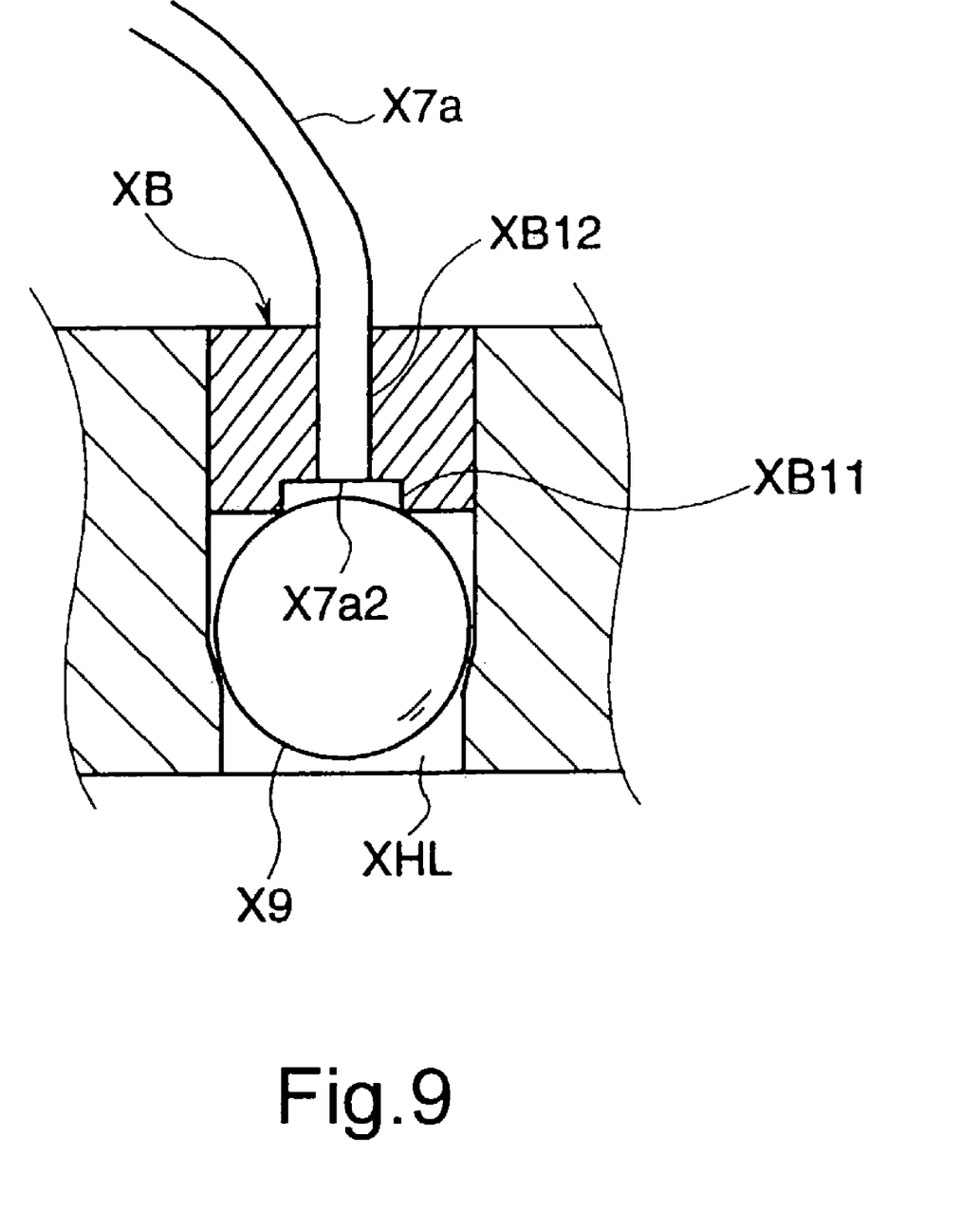
FIG. 9 is a fragmentary sectional view of an illuminating unit according to yet another variation of the same embodiment.

The fusion-deformed portion is not necessarily needed. Any arrangement capable of precisely and easily setting the distance between the light-emitting end of the optical fiber and the lens can produce the essential effect of the present invention. A conceivable example of such an arrangement is such that: the equal-diameter portion holds the optical fiber extending therethrough with the light-emitting end thereof coinciding with the forward end of the equal-diameter portion; and the lens is abutted against one end face of the fiber holding portion. Specific examples of such an arrangement include one shown in FIG. 9 wherein lens X9 is abutted against the peripheral edge defining the opening of larger-diameter portion XB11 with a portion of the lens X9 protruding into the larger-diameter portion XB11. In this case any jig can be used to make the light-emitting end X7a of the optical fiber X7a coincide with the forward end of the equal-diameter portion XB12 and the optical fiber X7a can be held with use of adhesive or the like.

It is possible that the lens holding hole has a sectional configuration other than a circular configuration while the shape of the fiber holding portion is changed to meet the sectional configuration of the lens holding hole.

Figure 13:
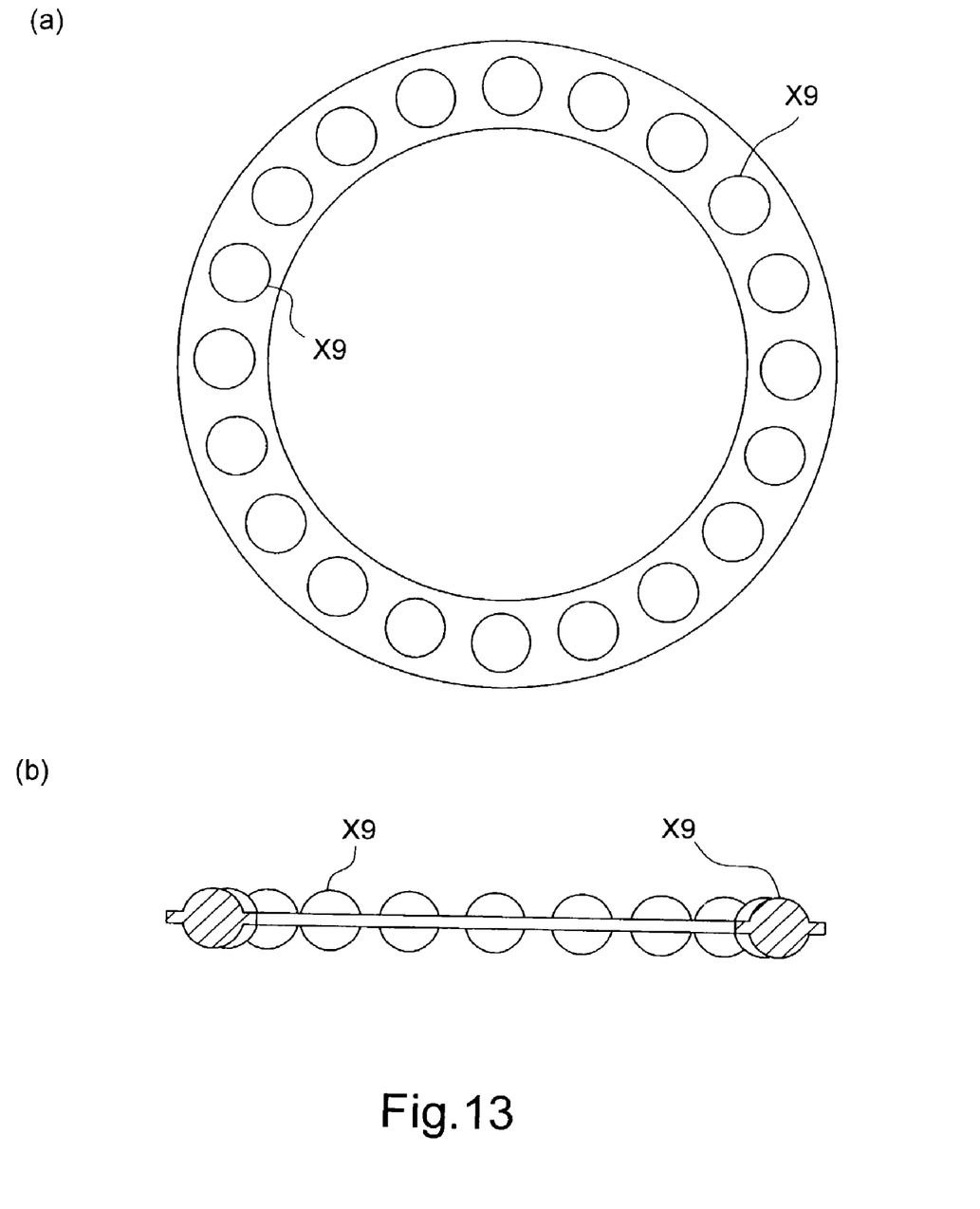
FIGS. 13(a) and 13(b) are a top plan view and a central vertical sectional view, respectively, of a lens according to a yet still further variation of the same embodiment.

As shown in FIG. 13, the ball lenses X9 may not be separated from each other and may form an integral ring having a thin plate interconnecting the spherical surfaces of respective ball lenses. In this case the ball lenses X9 are physically interconnected, but are considered to have their respective independent functions with respect to corresponding optical fibers. Though the shape of each lens is not limited to a spherical ball shape, a spherical lens is suitable for assemblage because it can be fitted into the lens holding hole without the need to take the posture thereof into consideration.

Figure 10:
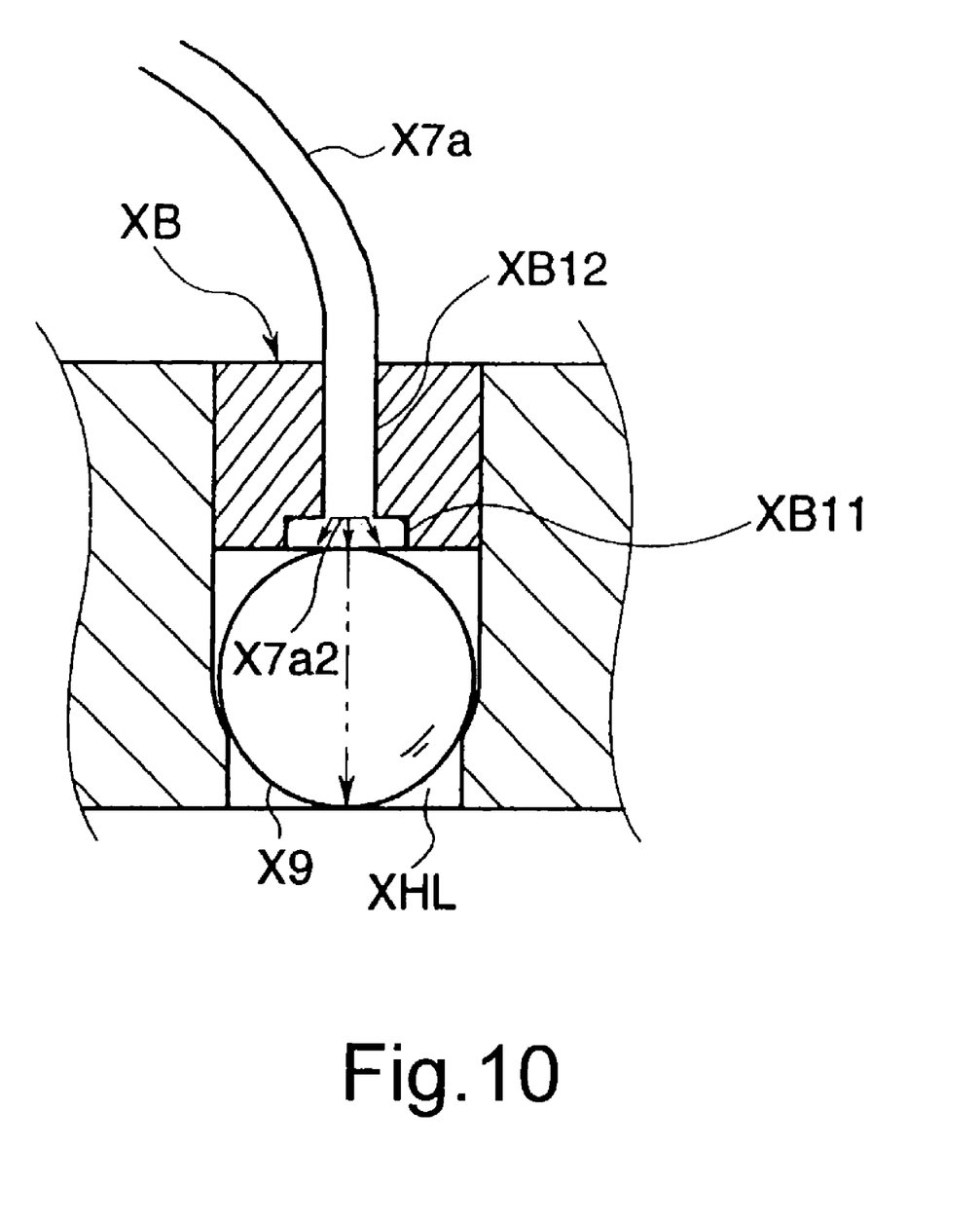
FIG. 10 is a fragmentary sectional view of an illuminating unit according to still yet another variation of the same embodiment.
Figure 11:
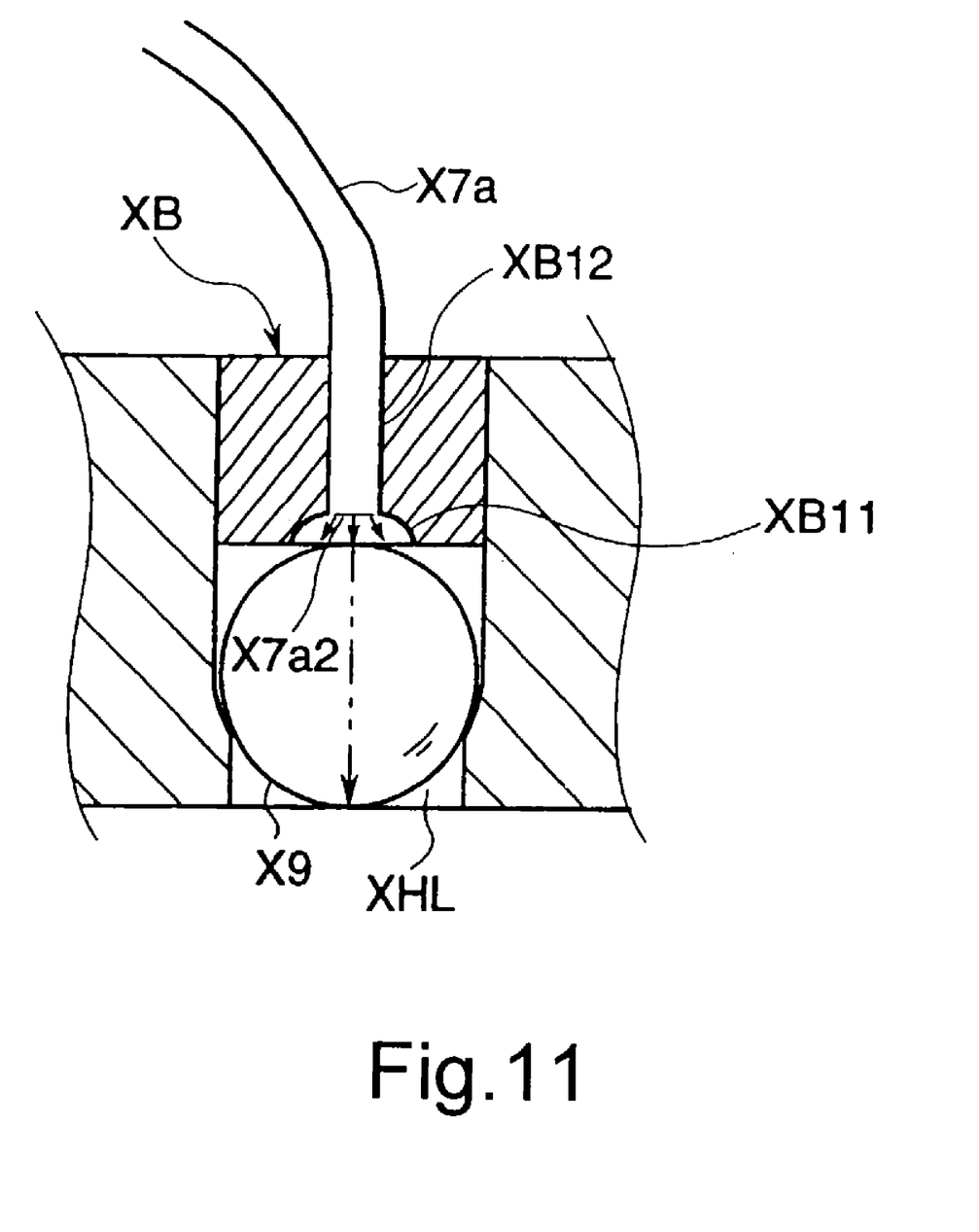
FIG. 11 is a fragmentary sectional view of an illuminating unit according to a further variation of the same embodiment.

The larger-diameter portion may be shaped, for example, into a cylindrical concave as shown in FIG. 10 or a fragmentary spherical concave as shown in FIG. 11, instead of a conical concave. That is, the larger-diameter portion is preferably shaped to have an inner periphery kept clear of light that is emitted divergently from the light-emitting end.

Where the lens has a larger diameter, the diameter of the lens holding hole for holding the lens becomes larger accordingly. However, the fiber holding portion requires relatively precise machining for its shaping and must permit the optical fiber to be inserted therethrough and, hence, changing the shape of the fiber holding portion to meet the lens holding hole imposes a burden on the production equipment and is not preferable even from the view point of cost and the like.

Figure 12:
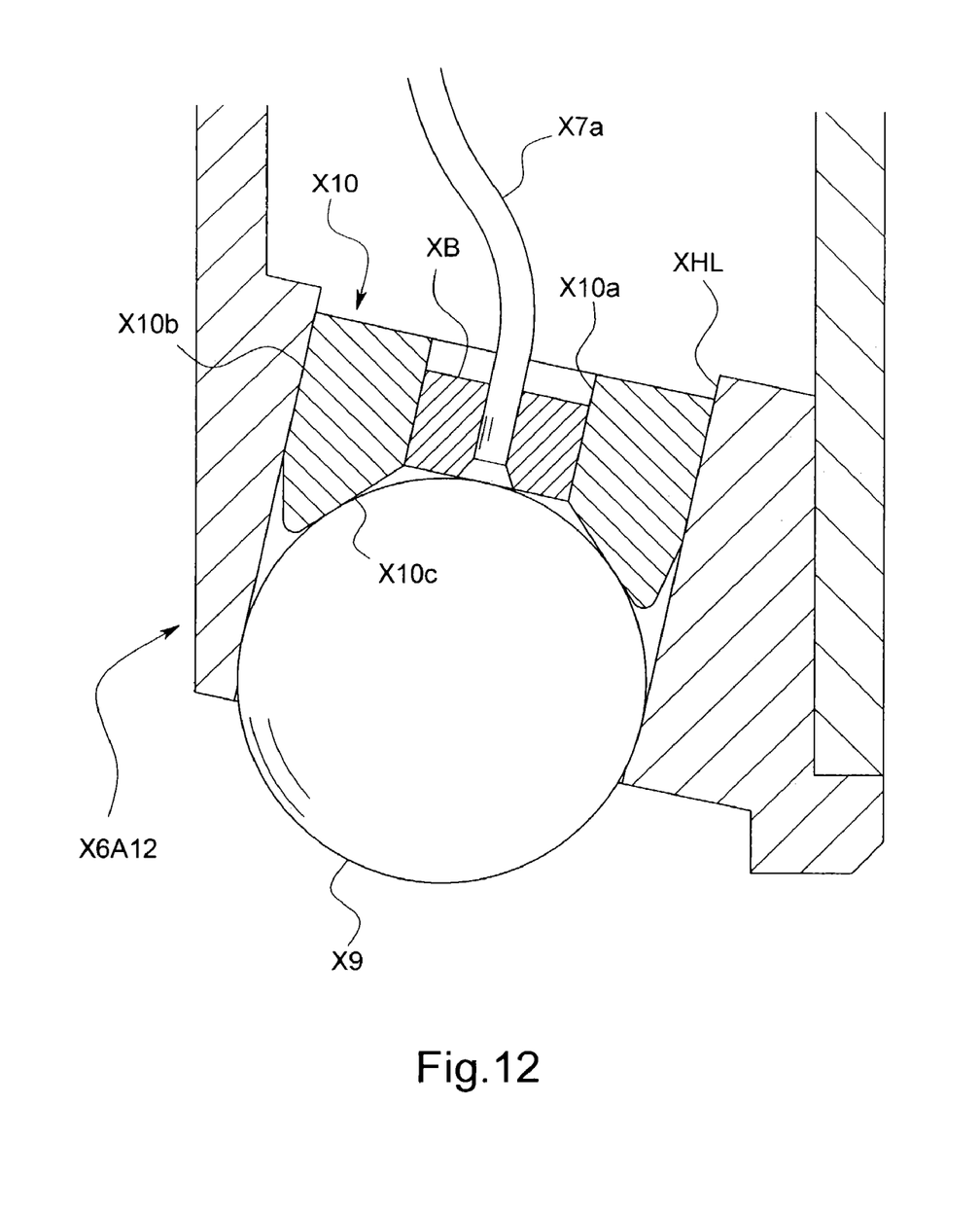
FIG. 12 is a fragmentary sectional view of an illuminating unit according to a still further variation of the same embodiment.

For this reason, where the fiber holding portion XB has a smaller diameter than the lens holding hole XHL, the illuminating unit may further comprise a cylindrical adapter X10 having an inner periphery X10a capable of fitting around the fiber holding portion XB without play therebetween and an outer periphery X10b capable of fitting into the lens holding hole XHL without play therebetween, as shown in FIG. 12. The adapter X10 shown has a cylindrical shape and is formed with a tapered surface X10c defining a truncated conical concave on the target portion side. The tapered surface X10c abuts the lens X9 without play therebetween and serves to fix the lens X9 firmly.

While only certain presently preferred embodiments of the present invention have been described in detail, as will be apparent for those skilled in the art, certain changes and modifications may be made in embodiments without departing from the spirit and scope of the present invention as defined by the following claims.

What is claimed is:

1. An illuminating unit for illuminating a target portion of an object to be illuminated, comprising:
    a fiber holding portion having a fiber insert hole holding a light-emitting end portion of an optical fiber;
    a lens;
    a lens located downstream of the fiber holding portion in a light traveling direction, light emitted from a light-emitting end of the optical fiber being directed to the target portion through the lens held by the lens holding portion, wherein:
    the fiber insert hole comprises an equal-diameter portion having a diameter substantially equal to a diameter of the optical fiber, and a larger-diameter portion having a larger diameter than the equal-diameter portion at an opening on one end face of the fiber holding portion, the fiber insert hole having the optical fiber extending through the equal-diameter portion; and
    the lens is abutted against the one end face of the fiber holding portion or a forward end face of a fusion-deformed portion of the optical fiber, the fusion-deformed portion being fitted in the larger-diameter portion and resulting from fusion deformation of a leading end portion of the optical fiber projecting from the equal-diameter portion to prevent withdrawal of the optical fiber from the fiber holding portion.

2. The illuminating unit in accordance with claim 1, wherein the larger-diameter portion is shaped to have an inner periphery clear of light that is divergently emitted from the light-emitting end of the optical fiber.

3. The illuminating unit in accordance with claim 1, wherein: the lens holding portion has a lens holding hole accommodating and holding the lens therein; and the fiber holding portion is shaped columnar having a sectional configuration the same as the lens holding hole and defining the fiber insert hole axially extending therethrough, the fiber holding portion being fitted in the lens holding hole holding the lens on a side opposite away from the target portion in a manner to abut the lens against the forward end face of the fusion-deformed portion or the one end face of the fiber holding portion.

4. The illuminating unit in accordance with claim 1, further comprising a cylindrical adapter having an inner periphery capable of fitting around the fiber holding portion without play therebetween and an outer periphery capable of fitting into the lens holding hole without play therebetween, provided the fiber holding portion has a smaller diameter than the lens holding hole.

5. The illuminating unit in accordance with claim 4, wherein the adapter is formed with a tapered surface for abutting and fixing the lens on a side closer to the target portion.

6. The illuminating unit in accordance with claim 1, further comprising an enclosure defining a plurality of discrete fiber insertion holes holding respective optical fibers, the lens holding portion holding a plurality of lenses in a one-to-one correspondence with the optical fibers.

7. The illuminating unit in accordance with claim 6, further comprising a single second lens for refracting light rays outgoing from the respective lenses to gather the light rays onto the target portion, the second lens being located between the plurality of lenses and the target portion and having an annular shape defining a central hole extending therethrough.

8. The illuminating unit in accordance with claim 1, wherein the lens holding portion has a ring shape defining a plurality of discrete lens holding holes located circumferentially.

9. The illuminating unit in accordance with claim 1, wherein the lens held by the lens holding portion is shaped spherical.

10. An illuminating unit for directing light from a source to a target surface comprising:
    an optical fiber having a first end for receiving light and a second end for releasing light;
    an optical fiber holding portion having a bore extending therethrough of a first diameter for supporting the optical fiber, the bore connected to an enlarged opening of a dimension greater than the first diameter, the second end of the optical fiber having a dimension greater than the first diameter and complinentary to the enlarged opening for securing the optical fiber to the optical fiber holding portion;
    a lens holding portion operatively mounted adjacent to the optical fiber holding portion; and
    a lens mounted in the lens holding portion for operative contact with the second end of the optical fiber to direct any emitted light.

11. The illuminating unit in accordance with claim 10 further including a ring shaped holding member for supporting a plurality of optical fibers, optical fiber holding portions, lens holding portions and lenses that collectively provide an annular ring of light to the target surface.

12. The illuminating unit in accordance with claim 11 wherein the annular ring of light is angled inward towards an optical axis of the illuminating unit.

13. The illuminating unit in accordance with claim 10 wherein the lens holding portion includes a body having a bore of a dimension to support and hold the lens and support and hold the optical fiber holding portion operatively adjacent to the lens.

* * * * *